United States Patent [19]
Powell

[11] Patent Number: 5,263,468
[45] Date of Patent: Nov. 23, 1993

[54] CAMPFIRE HEAT INTENSIFIER

[76] Inventor: Stephen R. Powell, 577 Godwin Ave., Midland Park, N.J. 07432-1452

[21] Appl. No.: 901,208

[22] Filed: Jun. 19, 1992

[51] Int. Cl.$^5$ .............................................. A61F 7/00
[52] U.S. Cl. .................................. 126/204; 126/696; 135/87; 359/847
[58] Field of Search .................. 126/204, 30, 205, 697, 126/682, 29, 275, 696, 684, 680, 274; 359/350, 847, 871; 135/87, 900, 901

[56] References Cited

U.S. PATENT DOCUMENTS

| | | | |
|---|---|---|---|
| 42,879 | 5/1864 | Savier | 126/30 |
| 2,543,115 | 2/1951 | Lindstaedt | 126/274 |
| 2,675,807 | 4/1954 | Pursel | 128/372 |
| 2,757,664 | 8/1956 | McDowell | 126/275 |
| 2,798,478 | 7/1957 | Tarcici | 126/682 |
| 3,067,737 | 12/1962 | Brown | 126/274 |
| 3,463,577 | 8/1969 | Friedberg | 128/372 |
| 3,498,587 | 3/1970 | Friedberg | 544/101 |
| 3,574,447 | 4/1971 | Ruble | 359/847 |
| 3,898,980 | 8/1975 | Reimann | 126/274 |
| 3,978,533 | 9/1976 | Warner | 5/327 R |
| 4,981,152 | 1/1991 | Laurent | 135/117 |
| 4,996,970 | 3/1991 | Legare | 126/204 |

Primary Examiner—J. Yeung
Attorney, Agent, or Firm—Samuelson & Jacob

[57] ABSTRACT

A heat intensifier for directing radiant heat from a campfire toward a camper situated on the ground adjacent the campfire to enhance the warmth provided by the campfire to the camper includes a collapsible screen having a heat-reflective surface and a frame for attachment to the screen to deploy the screen in a concave-convex configuration in which the heat-reflective surface is located in a position relative to the camper and the campfire to reflect radiated heat from the campfire toward the camper, and anchoring devices for anchoring the attached screen and frame to the ground in that position.

11 Claims, 2 Drawing Sheets

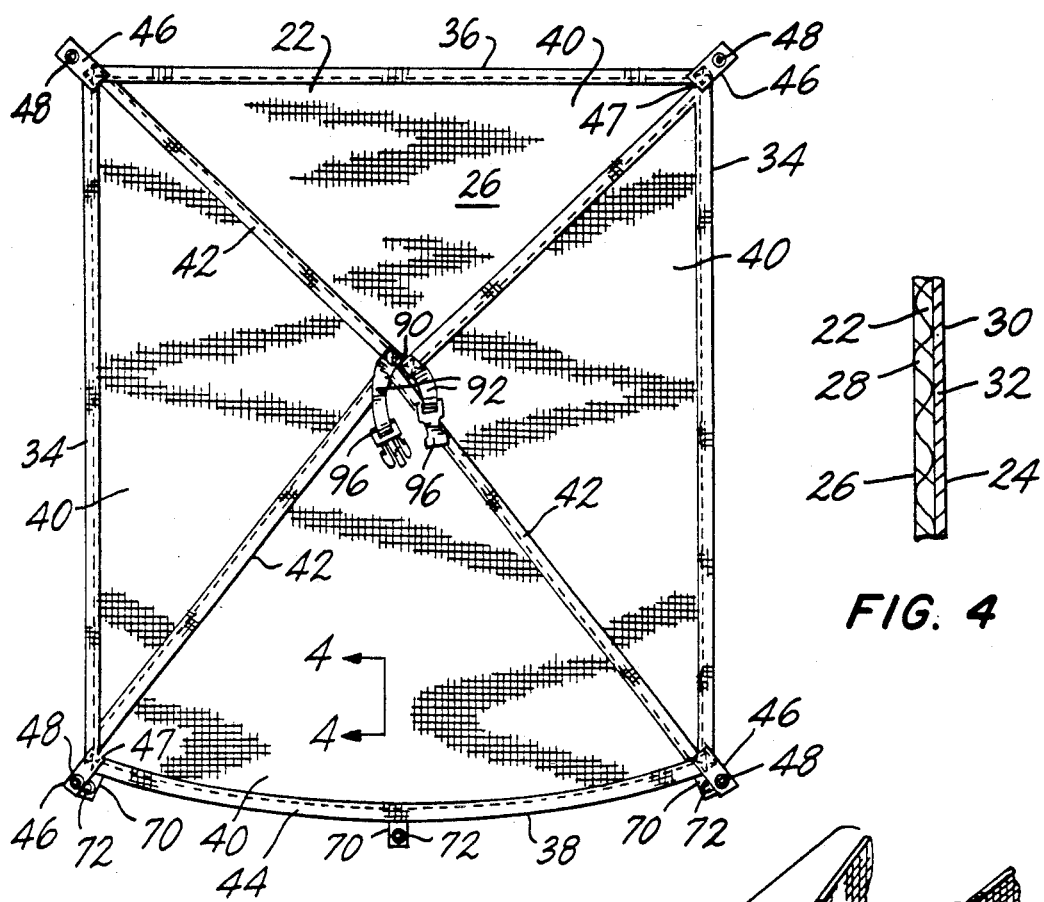
FIG. 3
FIG. 4
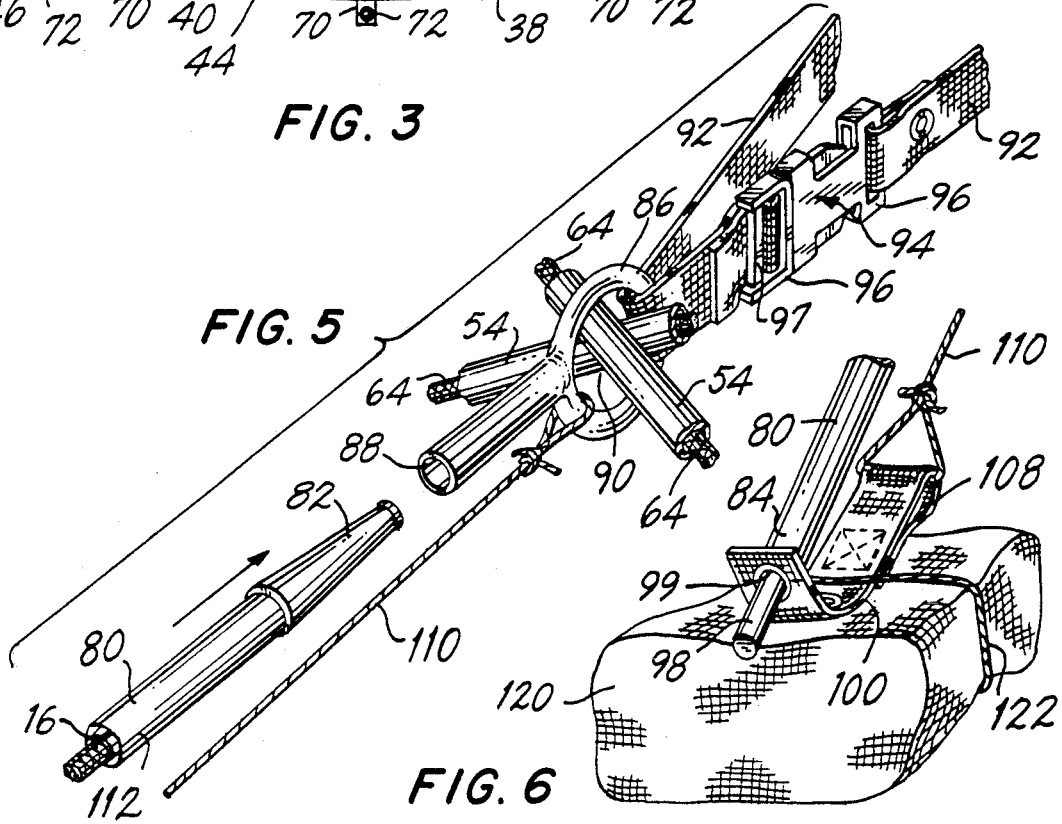
FIG. 5
FIG. 6

CAMPFIRE HEAT INTENSIFIER

The present invention relates generally to camping equipment and pertains, more specifically, to a collapsible, portable campfire heat intensifier for conserving the heat of a campfire and directing radiant heat of the campfire toward a camper.

Camping is becoming more popular as greater emphasis is placed upon preserving the natural environment and more people become aware of the enjoyment which can be derived from time spent in a natural setting. As a result, there has been an increased demand for camping equipment, and especially for lightweight portable items which easily are taken along on a camping trip and enhance the comfort of campers at a campsite.

One of the more enjoyable aspects of camping is the comfort derived from the use of a campfire. The warmth of a campfire often is a central attraction to camping and, in some instances, is a necessity for survival. However, although almost universally employed for warmth, a campfire, by its nature, is relatively inefficient in providing warmth to a camper. The present invention provides an item of camping equipment which renders a campfire more effective in directing heat to a camper. As such, the present invention exhibits several objects and advantages, some of which are summarized as follows: Provides an item of camping equipment which increases the effectiveness of a campfire in warming a camper by intensifying the heat directed to the camper from the campfire; enables a high degree of portability and ease of erection of equipment for enhancing the effectiveness of a campfire in warming a camper; provides a relatively sturdy and stable arrangement with a minimum number of component parts of relatively simple construction; requires very little by way of preparation of the campsite for effective use; provides a compact package, when dismantled, for ease of carrying in standard hiking and camping packs, yet is erected readily into a fully effective device which remains stable in use under the conditions encountered at the campsite; utilizes component parts which resist damage and deterioration under the conditions encountered in the field for enabling exemplary performance over a long service life.

The above objects and advantages, as well as further objects and advantages, are attained by the present invention which may be described briefly as a heat intensifier for directing radiant heat from a campfire toward a camper situated on the ground adjacent the campfire to enhance the warmth provided by the campfire to the camper, the heat intensifier comprising: a collapsible screen including a substrate of flexible, foldable material capable of being folded into a compact configuration, an obverse face, a reverse face and a heat-reflective surface on the obverse face; frame members for erection into an erected frame for juxtaposition with the reverse face of the screen; attachment means for attaching the erected frame to the screen adjacent the reverse face of the screen to assemble the frame in a bowed configuration with the screen and deploy the screen in an erect arrangement wherein the deployed screen follows a concave-convex configuration with the obverse face following a concave surface contour and the reverse face following a convex surface contour; and foundation means for anchoring the assembled erected frame and deployed screen in a anchored position on the ground relative to the campfire and the camper wherein the heat-reflective surface on the obverse face of the screen will reflect radiant heat from the campfire toward the camper.

The invention will be understood more fully, while still further objects and advantages will become apparent, in the following detailed description of preferred embodiments of the invention illustrated in the accompanying drawing, in which:

FIG. is a pictorial view illustrating a campfire heat intensifier constructed in accordance with the present invention in use in connection with a campfire;

FIG. 3 is a rear elevational view of a component part of the heat intensifier;

FIG. 4 is an enlarged fragmentary cross-sectional view taken along line 4—4 of FIG. 3;

FIG. 5 is an exploded fragmentary view, in perspective, illustrating component parts being assembled; and FIG. 6 is an enlarged fragmentary pictorial view showing an alternate arrangement.

Figure 1:
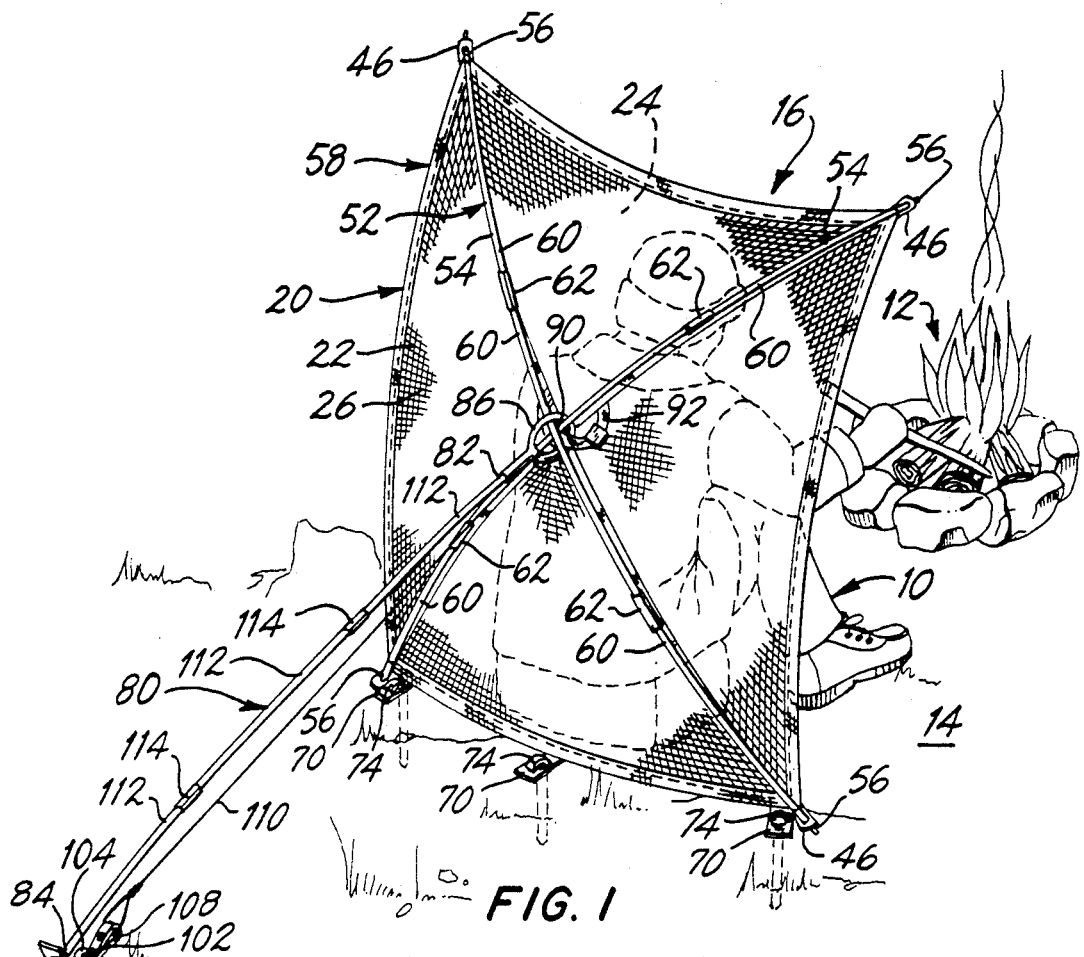

Referring now to the drawing, and especially to FIG. 1 thereof, a camper 10 is seen to be seated before a campfire 12 which is providing warmth to the camper 10. The camper 10 is seated on the ground 14 at a campsite 16 and is facing the campfire 12. A heat intensifier constructed in accordance with the present invention is depicted generally at 20 and is placed on the ground 14 and behind the camper 10 so as to be in position to reflect radiant heat from the campfire 12 toward the camper 10.

Figure 2:
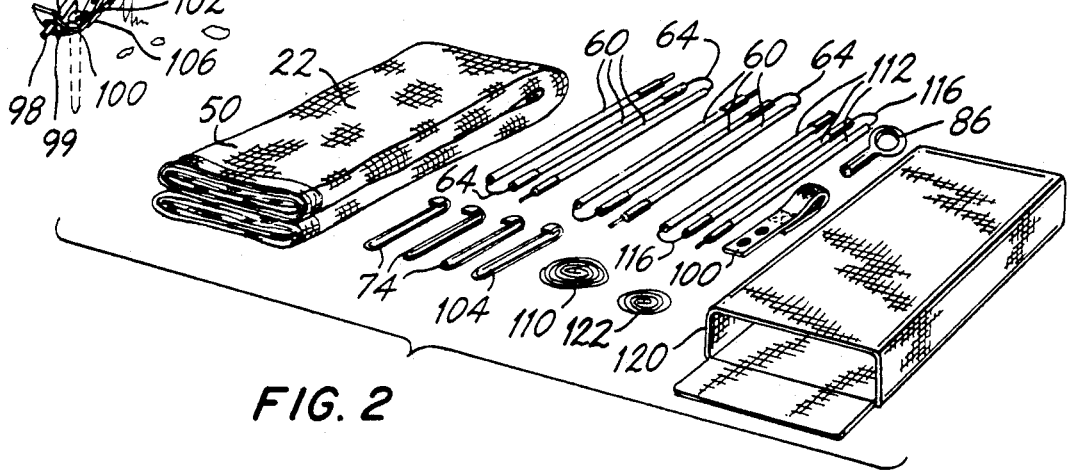
FIG. 2 is a pictorial view of the heat intensifier dismantled for transport or storage.

As best seen in FIGS. 2 through 4, as well as in FIG. 1, heat intensifier 20 includes a screen 22 having an obverse face 24 and a reverse face 26. Screen 22 is collapsible and has a substrate 28 constructed of a relatively lightweight flexible, foldable fabric, preferably selected from any one of a variety of synthetic polymeric fabrics including rayon, nylon, polyester and various blends of such fabrics. Obverse face 24 includes a heat-reflective surface 30, preferably provided by a layer 32 of heat-reflective material, such as aluminum, laminated to or otherwise deposited on the substrate 28. Thus, the preferred material for screen 22 is referred to as an aluminized fabric. Screen 22 has a generally rectangular overall plan configuration, with essentially straight peripheral side edges 34 and top edge 36. However, a base edge 38 is somewhat arcuate for purposes which will be explained in greater detail below. Screen 22 is constructed of four sectors 40 joined together as by sewn reinforcing seams 42 so that the screen 22 may take on a specific contour configuration, as will be explained hereinafter. A reinforcing hem 44 extends around the periphery of the screen 22 and a tab 46 is affixed to the screen 22 at each corner 47 of the screen. Each tab 46 has a grommeted aperture 48. The construction of screen 22 enables the screen 22 to be folded into a very compact configuration, as illustrated at 50 in FIG. 2, for portability and ease of storage.

A frame 52, as seen in FIG. 1, is erected from frame members 54 and is juxtaposed with the reverse face 26 of the screen 22. Each frame member 54 has a stepped tip 56 at each end of the frame member 54, which stepped tip 56 is inserted into a corresponding grommeted aperture 48 to assemble the frame 52 with the screen 22 in a manner now well known in the construction of tents and like enclosures. The frame members 54 follow a generally X-shaped array oriented so that each frame member 54 follows a diagonal across the screen 22 and each stepped tip 56 is placed at a corresponding grommeted aperture 48. The relation between the length of each frame member 54 and the distance between diagonally opposite grommeted apertures 48 is such that upon such assembly of the frame 52 with the screen 22, the frame 52 will be bowed and the screen 22 will be deployed into a concave-convex configuration, with the obverse face 24 following a concave surface contour and the reverse face 26 following a convex surface contour, as depicted in FIG. 1, with corresponding stepped tips 56 and grommeted apertures 48 serving as attachment means to attach the erected bowed frame 52 to the screen 22 adjacent the reverse face 26, thereby establishing assembly 58 comprising the bowed frame 52 and the deployed screen 22. The frame members 54 are constructed of longitudinally extending segments 60 joined together by ferrules 62, each segment 60 preferably being constructed of a somewhat stiff but flexible material, such as a reinforced polyester tube, all in a manner well known in the construction of tent poles and the like. Preferably, the tubular segments 60 of each frame member 54 are strung together by a common elastic cord 64 which is threaded longitudinally through the tubular segments 60 and is secured to the tubular segment 60 in such a way as to bias the segments 60 together in an erected frame member 54. In addition, the segments 60 of each frame member 54 are urged together by the forces exerted upon the opposite ends of the frame member 54 by the tension in the engaged deployed screen 22. The segments 60, when disengaged, are placed readily into a compact package, as seen in FIG. 2, with the segments 60 of each frame member 54 strung together with a respective common elastic cord 64.

Foundation means are provided in the form of base tabs 70 affixed to the screen 22 along the base edge 38 of the screen 22, as by sewing the base tabs 70 to the screen 22 at spaced locations along the base edge 38. Each base tab 70 serves as an anchoring means and includes an opening 72 for receiving a ground spike 74 for anchoring the assembly 58, which includes the erected frame 52 and deployed screen 22, in the position behind the camper 10, as shown in FIG. 1. The arcuate form of the base edge 38 assures that the base edge 38 is essentially contiguous with the ground 14 when the screen 22 is deployed in the concave-convex configuration so that the ground spikes 74 are effective in anchoring the assembly 58 and assist in maintaining the desired concave-convex configuration in the deployed screen 22.

In order to maintain the assembly 58 erect in the appropriate position behind the camper 10, an elongate stabilizer bar 80 is secured to the assembly 58, behind the screen 22. Stabilizer bar 80 includes a proximal end 82 and a distal end 84. Coupling means are provided for coupling and securing the proximal end 82 of the stabilizer bar 80 to the assembly 58. To this end, a ring 86 is joined to the proximal end 82 of the stabilizer bar 80 by a socket 88 integral with the ring 86. The frame members 54 are passed through the ring 86 at a datum location 90 at the intersection of the frame members 54. The coupling means further include strap elements 92 attached to the screen 22 adjacent the datum location 90, as by sewing the strap elements 92 to the screen 22 along the reinforcing seams 42. At least one of the strap elements 92 is passed through the ring 86, as seen in FIG. 5, and a buckle 94 having buckle elements 96 carried by the strap elements 92, is fastened to secure the screen 22 to the proximal end 82 of the stabilizer bar 80 so that the stabilizer bar 80 is secured firmly to the assembly 58, with the strap elements 92 serving to pull the screen 22, adjacent the datum location 90, toward the frame 52 so as to assist in maintaining the desired concave-convex configuration in screen 22. A selectively adjustable connection at 97 between corresponding strap element 92 and buckle element 96 enables selective adjustment of the position of the deployed screen 22 relative to the erected frame 52 at the datum location 90.

As best seen in FIG. 1, the distal end 84 of the stabilizer bar 80 includes a stepped tip 98 which is received within a grommeted aperture 99 of a further foundation means shown in the form of a strap 100 having an opening 102 through which a ground spike 104 extends to be driven into the ground 14 for anchoring the strap 100. The strap 100 is anchored to the ground 14 at a location 106 spaced away from the screen 22 in the direction extending from the reverse face 26 away from the campfire 12. Strap 100 includes a loop 108, and a tension cord 110 is tied between the loop 108 and the ring 86 to bias the stepped tip 98 into appropriate coupled engagement with the grommeted aperture 99, under the conditions encountered at the campsite 16. In the preferred construction, stabilizer bar 80 is constructed of segments 112 in the form of more rigid tubular members secured together at ferrules 114, utilizing a common elastic cord 116 threaded longitudinally through the segments 112 and secured to the segments 112 in much the same manner as the arrangement between frame members 54 and respective elastic cords 64, and is broken down for transport or storage, as shown in FIG. 2. The tension cord 110, when tied between loop 108 and ring 86, assists in retaining the segments 112 assembled in stabilizer bar 80 against wind and other forces which may tend to place stabilizer bar 80 in tension. In an alternate arrangement, as illustrated in FIG. 6, ground spike 104 is replaced by an anchor in the form of a sack 120 weighted down with materials indigenous to the campsite 16, such as stones, and tied to the strap 100 by an anchoring line 122. As seen in FIG. 2, sack 120 also may serve as a packaging means for the component parts of the heat intensifier 20, when dismantled for transport and for storage. Alternately, anchoring line 122 may be tied to a rock or another weighted item found at the campsite 16.

When erected in the manner illustrated in FIG. heat intensifier 20 is placed behind the camper 10 so that radiant heat from the campfire 12 is reflected by the concave contoured heat-reflective surface 30 to the camper 10, rather than being dissipated into the ambient atmosphere. In this manner, the heat of campfire 12 is conserved and campfire 12 is rendered more effective in warming the camper 10 as well as more efficient. When broken down into separate relatively lightweight component parts, the heat intensifier 20 is packed in a compact configuration which adds very little weight to be carried by the camper 10 and requires very little carrying space. The configuration of the heat intensifier 20 and the construction of the component parts enables the number and the weight of the parts to be minimized for ease of portability, while providing an erected device capable of withstanding the rigors of outdoor use under the conditions encountered at the campsite.

It will be seen that the present invention attains the objects and advantages summarized above, namely: Provides an item of camping equipment which increases the effectiveness of a campfire in warming a camper by intensifying the heat directed to the camper from the campfire; enables a high degree of portability and ease of erection of equipment for enhancing the effectiveness of a campfire in warming a camper; provides a relatively sturdy and stable arrangement with a minimum number of component parts of relatively simple construction; requires very little by way of preparation of the campsite for effective use; provides a compact package, when dismantled, for ease of carrying in standard hiking and camping packs, yet is erected readily into a fully effective device which remains stable in use under the conditions encountered at the campsite; utilizes component parts which resist damage and deterioration under the conditions encountered in the field for enabling exemplary performance over a long service life.

It is to be understood that the above detailed description of preferred embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. A heat intensifier for directing radiant heat from a campfire toward a camper situated on the ground adjacent the campfire to enhance the warmth provided by the campfire to the camper, the heat intensifier comprising:
    a collapsible screen including a substrate of flexible, foldable material capable of being folded into a compact configuration, an obverse face, a reverse face and a heat-reflective surface on the obverse face;
    frame members for erection into an erected frame for juxtaposition with the reverse face of the screen;
    attachment means for attaching the erected frame to the screen adjacent the reverse face of the screen to assemble the frame in a bowed configuration with the screen and deploy the screen in an erect arrangement wherein the deployed screen follows a concave-convex configuration with the obverse face following a concave surface contour and the reverse face following a convex surface contour; and
    foundation means for anchoring the assembled erected frame and deployed screen in an anchored position on the ground relative to the campfire and the camper wherein the heat-reflective surface on the obverse face of the screen will reflect radiant heat from the campfire toward the camper;
    the screen including a peripheral base edge having a somewhat arcuate configuration for lying essentially contiguous with the ground when the assembled erected frame and deployed screen are in the anchored position; and
    the foundation means including anchoring means located at the peripheral base edge for anchoring the assembled erected frame and deployed screen to the ground at the peripheral base edge to assist in maintaining the concave-convex configuration of the deployed screen.

2. The invention of claim 1 wherein the screen is constructed of sectors of material joined together to enable deployment of the screen in the concave-convex configuration.

3. The invention of claim 1 wherein the screen is constructed of an aluminized fabric.

4. A heat intensifier for directing radiant heat from a campfire toward a camper situated on the ground adjacent the campfire to enhance the warmth provided by the campfire to the camper, the heat intensifier comprising:
    a collapsible screen including a substrate of flexible, foldable material capable of being folded into a compact configuration, an obverse face, a reverse face and a heat-reflective surface on the obverse face;
    frame members for erection into an erected frame for juxtaposition with the reverse face of the screen;
    attachment means for attaching the erected frame to the screen adjacent the reverse face of the screen to assemble the frame in a bowed configuration with the screen and deploy the screen in an erect arrangement wherein the deployed screen follows a concave-convex configuration with the obverse face following a concave surface contour and the reverse face following a convex surface contour;
    foundation means for anchoring the assembled erected frame and deployed screen in an anchored position on the ground relative to the campfire and the camper wherein the heat-reflective surface on the obverse face of the screen will reflect radiant heat from the campfire toward the camper;
    an elongate stabilizer bar having a proximal end and a distal end;
    coupling means for coupling the proximal end of the stabilizer bar to the erected frame such that the bar projects in a direction away from the campfire to place the distal end at a location spaced away from the reverse face of the screen in the direction away from the campfire; and
    further foundation means for anchoring the distal end of the stabilizer bar to maintain the assembled erected frame and deployed screen in place.

5. The invention of claim 4 wherein the erected frame comprises first and second frame members in a generally X-shaped array and intersecting one another at a datum location.

6. The invention of claim 5 wherein the coupling means is located adjacent the datum location so as to enable coupling of the proximal end of the stabilizer bar with the erected frame essentially at the datum location.

7. The invention of claim 6 wherein the coupling means includes a ring at the proximal end of the stabilizer bar and the frame members of the erected frame pass through the ring at the datum location.

8. The invention of claim 7 wherein the coupling means includes strap elements secured to the deployed screen adjacent the datum location and extending through the ring to pull the deployed screen toward the erected frame adjacent the datum location and assist in urging the deployed screen into the concave-convex configuration.

9. The invention of claim 6 including a tension cord for being tied between the proximal end of the stabilizer bar and the further foundation means to bias the stabilizer bar toward the further foundation means.

10. The invention of claim 9 wherein the stabilizer bar includes longitudinally extending tubular segments, ferrules for joining the tubular segments together, and a common elastic cord passing longitudinally through the tubular segments to bias the tubular segments together in the stabilizer bar.

11. The invention of claim 9 wherein the further foundation means includes an aperture for receiving the distal end of the stabilizing bar to couple the stabilizer bar with the further foundation means.

* * * * *